US009808468B2

(12) United States Patent
Bosch

(10) Patent No.: US 9,808,468 B2
(45) Date of Patent: *Nov. 7, 2017

(54) FORMULATION OF MELOXICAM

(71) Applicant: ICEUTICA PTY LTD., Balcatta, WA (US)

(72) Inventor: H. William Bosch, Bryn Mawr, PA (US)

(73) Assignee: iCeutica Pty Ltd., Iluka, WA (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/595,446

(22) Filed: May 15, 2017

(65) Prior Publication Data

US 2017/0246178 A1     Aug. 31, 2017

Related U.S. Application Data

(63) Continuation of application No. 14/974,108, filed on Dec. 18, 2015, now Pat. No. 9,649,318, which is a continuation of application No. 14/675,410, filed on Mar. 31, 2015, now Pat. No. 9,526,734.

(60) Provisional application No. 62/009,860, filed on Jun. 9, 2014.

(51) Int. Cl.
| A61K 31/5415 | (2006.01) |
| A61K 31/00 | (2006.01) |
| A61K 9/16 | (2006.01) |
| A61K 9/14 | (2006.01) |

(52) U.S. Cl.
CPC .......... *A61K 31/5415* (2013.01); *A61K 9/145* (2013.01); *A61K 9/1617* (2013.01); *A61K 9/1623* (2013.01); *A61K 9/1652* (2013.01)

(58) Field of Classification Search
None
See application file for complete search history.

(56) References Cited

U.S. PATENT DOCUMENTS

| 3,172,546 | A | 3/1965 | Schreiner |
| 4,133,814 | A | 1/1979 | Jones et al. |
| 4,200,361 | A | 4/1980 | Malvano et al. |
| 4,380,635 | A | 4/1983 | Peters |
| 4,418,068 | A | 11/1983 | Jones |
| 4,606,909 | A | 8/1986 | Bechgaard et al. |
| 4,607,517 | A | 8/1986 | Finzer et al. |
| 5,145,684 | A | 9/1992 | Liversidge et al. |
| 5,202,129 | A | 4/1993 | Samejima et al. |
| 5,298,262 | A | 3/1994 | Na et al. |
| 5,470,583 | A | 11/1995 | Na et al. |
| 5,478,705 | A | 12/1995 | Czekai et al. |
| 5,500,331 | A | 3/1996 | Czekai et al. |
| 5,510,118 | A | 4/1996 | Bosch et al. |
| 5,518,187 | A | 5/1996 | Bruno et al. |
| 5,534,270 | A | 7/1996 | De Castro |
| 5,591,456 | A | 1/1997 | Franson et al. |
| 6,165,506 | A | 12/2000 | Jain et al. |
| 6,316,026 | B1 | 11/2001 | Tatara et al. |
| 6,316,029 | B1 | 11/2001 | Jain et al. |
| 6,428,814 | B1 | 8/2002 | Bosch et al. |
| 6,462,093 | B1 | 10/2002 | Miyamoto et al. |
| 6,634,576 | B2 | 10/2003 | Verhoff et al. |
| 6,713,494 | B1 | 3/2004 | Cuff et al. |
| 6,811,767 | B1 | 11/2004 | Bosch et al. |
| 6,894,064 | B2 | 5/2005 | Arbuthnot et al. |
| 6,908,626 | B2 | 6/2005 | Cooper et al. |
| 7,101,576 | B2 | 9/2006 | Hovey et al. |
| 7,714,006 | B1 | 5/2010 | Scaife et al. |
| 7,750,165 | B2 | 7/2010 | Chattopadhyay et al. |
| 9,526,734 | B2 | 12/2016 | Bosch |
| 9,649,318 | B2 | 5/2017 | Bosch |
| 2002/0012675 | A1 | 1/2002 | Jain et al. |
| 2002/0047058 | A1 | 4/2002 | Verhoff et al. |
| 2003/0137067 | A1 | 7/2003 | Cooper et al. |
| 2003/0216457 | A1 | 11/2003 | Scaife et al. |
| 2004/0022846 | A1 | 2/2004 | Depui et al. |
| 2004/0037785 | A1 | 2/2004 | Staniforth et al. |
| 2004/0057993 | A1 | 3/2004 | Jain et al. |
| 2004/0058009 | A1 | 3/2004 | Ryde et al. |
| 2004/0121003 | A1 | 6/2004 | Chickering, III et al. |
| 2004/0173696 | A1 | 9/2004 | Cunningham et al. |
| 2004/0229038 | A1 | 11/2004 | Cooper et al. |
| 2005/0013857 | A1 | 1/2005 | Fu et al. |
| 2005/0019412 | A1 | 1/2005 | Bosch et al. |
| 2005/0063913 | A1 | 3/2005 | Pruitt et al. |
| 2005/0163839 | A1 | 7/2005 | Dudhara et al. |

(Continued)

FOREIGN PATENT DOCUMENTS

| EP | 0371431 | 6/1990 |
| EP | 0670162 | 9/1995 |

(Continued)

OTHER PUBLICATIONS

Medication Guide for Non-Steroidal Anti-Inflammatory Drugs (Approved by the U.S. Food and Drug Administration Aug. 2007)("Medication Guide").
Rodriguez et al., Epidemiology, vol. 12 (Issue 5); pp. 570-576 (2001).
Dokoumetzidis et al., "A century of dissolution research: from Noyes and Whitney to the biopharmaceutics classification system," Int. J. of Pharm., 321(1-2):1-11 (2006).
Kesisoglou et al., "Nanosizing-oral formulation development and biopharmaceutical evaluation," Adv. Drug Deliv Rev., 59(7):631-644 (2007).
Turck et al., "A review of the clinical pharmacokinetics of meloxicam," Br. J. Rheumatol., vol. 35 (suppl. 1), pp. 13-16 (1996).
Notice of Paragraph IV Certification Regarding NDA 207233: Letter dated Jan. 9, 2017, pp. 1-42.

(Continued)

*Primary Examiner* — Bethany Barham
*Assistant Examiner* — Barbara Frazier
(74) *Attorney, Agent, or Firm* — Fish & Richardson P.C.

(57) ABSTRACT

Unit dosage forms of meloxicam containing either 5 mg or 10 mg of meloxicam that provide effective pain relief and have desirable pharmacokinetic properties are described. The unit dosage forms can provide pain relief when a single unit dose is administered to a patient and useful for treating pain such as osteoarthritis pain at a relatively low systemic exposure to meloxicam.

24 Claims, No Drawings

(56) References Cited

U.S. PATENT DOCUMENTS

| | | |
|---|---|---|
| 2005/0276844 A1 | 12/2005 | Spireas |
| 2006/0154966 A1 | 7/2006 | Karup et al. |
| 2006/0287346 A1 | 12/2006 | Van Schie |
| 2007/0185177 A1 | 8/2007 | Chattopadhyay et al. |
| 2008/0254128 A1 | 10/2008 | Zarkadas et al. |
| 2008/0292584 A1 | 11/2008 | Roberts |
| 2009/0028948 A1 | 1/2009 | Payne et al. |
| 2010/0016597 A1 | 1/2010 | Hirokawa et al. |
| 2010/0092563 A1 | 4/2010 | Raffaele et al. |
| 2010/0297252 A1 | 11/2010 | Cooper et al. |
| 2011/0086074 A1 | 4/2011 | Karatgi et al. |
| 2012/0135047 A1 | 5/2012 | Dodd et al. |
| 2012/0141548 A1 | 6/2012 | Dodd et al. |
| 2012/0148634 A1 | 6/2012 | Dodd et al. |
| 2012/0160944 A1 | 6/2012 | Dodd et al. |
| 2012/0165323 A1 | 6/2012 | Dodd et al. |
| 2012/0165410 A1 | 6/2012 | Dodd et al. |
| 2012/0202694 A1 | 8/2012 | Dodd et al. |
| 2012/0263760 A1 | 10/2012 | Dodd et al. |
| 2013/0209569 A1 | 8/2013 | Dodd et al. |

FOREIGN PATENT DOCUMENTS

| | | |
|---|---|---|
| EP | 0699672 | 3/1996 |
| EP | 0600528 | 6/2000 |
| EP | 1066825 | 1/2001 |
| JP | 2004/99442 | 4/2004 |
| WO | WO 97/02017 | 1/1997 |
| WO | WO 97/06781 | 2/1997 |
| WO | WO 98/35666 | 8/1998 |
| WO | WO 99/09988 | 3/1999 |
| WO | WO 00/13672 | 3/2000 |
| WO | WO 01/03670 | 1/2001 |
| WO | WO 02/00197 | 1/2002 |
| WO | WO 02/45684 | 6/2002 |
| WO | WO 02/056866 | 7/2002 |
| WO | WO 02/094215 | 11/2002 |
| WO | WO 03/000228 | 1/2003 |
| WO | WO 2004/019937 | 3/2004 |
| WO | WO 2004/041991 | 5/2004 |
| WO | WO 2004/058216 | 7/2004 |
| WO | WO 2004/060344 | 7/2004 |
| WO | WO 2005/000273 | 1/2005 |
| WO | WO 2005/002542 | 1/2005 |
| WO | WO 2005/004915 | 1/2005 |
| WO | WO 2005/013937 | 2/2005 |
| WO | WO 2005/016310 | 2/2005 |
| WO | WO 2005/020933 | 3/2005 |
| WO | WO 2005/032703 | 4/2005 |
| WO | WO 2005/044234 | 5/2005 |
| WO | WO 2006/009825 | 1/2006 |
| WO | WO 2006/031026 | 3/2006 |
| WO | WO 2006/041843 | 4/2006 |
| WO | WO 2006/060698 | 6/2006 |
| WO | WO 2006/009419 | 7/2006 |
| WO | WO 2006/069419 | 7/2006 |
| WO | WO 2006/116596 | 11/2006 |
| WO | WO 2006/133954 | 12/2006 |
| WO | WO 2007/001451 | 1/2007 |
| WO | WO 2007/070843 | 6/2007 |
| WO | WO 2007/070851 | 6/2007 |
| WO | WO 2007/070852 | 6/2007 |
| WO | WO2007/150075 | 12/2007 |
| WO | WO 2008/000042 | 1/2008 |
| WO | WO 2008/011830 | 1/2008 |
| WO | WO 2008/013416 | 1/2008 |
| WO | WO 2008/118331 | 10/2008 |
| WO | WO 2009/027337 | 3/2009 |
| WO | WO 2010/017104 | 2/2010 |
| WO | WO 2010/121320 | 10/2010 |
| WO | WO 2010/121321 | 10/2010 |
| WO | WO 2010/121322 | 10/2010 |
| WO | WO 2010/121323 | 10/2010 |
| WO | WO 2010/121324 | 10/2010 |
| WO | WO2010/0121325 | 10/2010 |
| WO | WO 2010/121326 | 10/2010 |
| WO | WO 2010/121327 | 10/2010 |
| WO | WO 2010/121328 | 10/2010 |
| WO | WO 2015/013336 | 1/2015 |

OTHER PUBLICATIONS

Bowen P., "Particle Size Distribution Measurement from Millimeters to Nanometers and from Rods to Platelets," Journal of Dispersion Science and Technology, 23(5):631-662 (2002).

Bahl et al. "Amorphization of Indomethacin by Co-Grinding with Neusiling US2: Amorphization Kinetics, Physical Stability and Mechanism," Pharmaceutical Research, (2006), vol. 23 (10), pp. 2317-2325.

Barzegar-Jalali et al. "Evaluation of in vitro-in vivo correlation and anticonvulsive effect of carbamazepine after cogrinding with microcrystalline cellulose" J Pharm Phannaceut Science (2006), vol. 9 (3), pp. 307-316. See abstract, pp. 308-313.

Diaz et al., "Micronization. Its technological application in the manufacture of finished pharmaceutical forms," Rev Cubana Farm., 2001, 35(3):159-164.

FDA, Naproxen-Patient I nformation Sheet. Dec. 23, 2004, 1 page.

Fukami et al. "A nanoparticle processing in solid state dramatically increases the cell membrane permeation of a cholesterol lowering drug", Mol. Pharmaceutics, 6 (3):1029-1035, 2009.

Grigorieva et al., "Mechanosynthesis of nanocomposites," Journal of Nanoparticle Research vol. 5, p. 439-453, 2003.

Gupta et al. "Formation of Physically Stable Amorphous Drugs by Milling with Neusilin," Journal of Pharmaceutical Sciences, (2003), vol. 92 (3), pp. 536-551.

Guterres et al., "Poly(D,L-lactide) nanocapsules containing non-steroidal anti-inflammatory drugs: gastrointestinal tolerance following intravenous and oral administration", Pharmaceutical Research, 12(10): 1545-1547, 1995.

Sharon Hertz, MD; NDA Approval letter, NDA No. 204592; reference ID 3392875; Deputy Director, Division of Anesthesia, Analgesia and Adduction Products, Office of Drug Evaluation II, Center for Drug Evaluation and Research; Oct. 18, 2013; 6 pages.

Juhnke et al: "Nanoparticles of soft materials by high-energy milling at low temperatures", 7th World Congress of Chemical Engineering, Glasgow, XP55031954, pp. 1-10, Jan. 2005.

Kondo, "Study related to design and development of high polymer prodrug by novel mechanochemical solid-state polymerization", Journal of Pharmaceutical Society of Japan, 120(12):1337-1346, 2000.

Kondo, "A Design and Development of Novel Polymeric Prodrugs Prepared by Mechanochemical Solid-State Polymerization," J Pharma Soc. JP, 2000, 120(12):1337-1346 (English abstract).

McCormick et al., "The Fundamentals of Mechanochemical Processing", Journal of Metals, vol. 50(11):61-65, 1998.

Nuguru, K., Giambattisto, D., and AI-Ghazawi, A. "Evaluation and Characterization of spray-dried Mannitol as an excipient for DC-formulations of Naproxen sodium." Merck. Sep. 2008, 2 pages.

Vogt et al., "Dissolution enhancement of fenofibrate by micronization, cogrinding and spray-drying: Comparison with commercial preparations," European Journal of Pharmaceutics and Biopharmaceutics, Elsevier Science Publishers B.Y., 68(2):283-288 Jan. 10, 2008.

Schaffazick et al., "Freeze-drying polymeric colloidal suspensions: nanocapsules, nanospheres and nanodispersion. A comparative study" European Journal of Pharmaceuticals and Biopharmaceuticals, 56(3): 501-505, 2003.

Jianrong et al., "Progress of research on nanodrugs," Chin J Schisto Control, 2006, 18(1):74-77.

Tsuzuki and McCormick, "Mechanochemical Synthesis of Metal Sulphide Nanoparticles," Nanostructured Materials, vol. 12 p. 75-78, 1999.

Tsuzuki and McCormick, "Mechanochemical synthesis of nanoparticles," Journal of Materials Science, vol. 39, p. 5143-5146, 2004.

Tsuzuki et al., "Mechanochemical Synthesis of Gadolinium Oxide Nanoparticles," Nanostructured Materials, vol. 11, No. 1, p. 125-131, 1999.

(56) References Cited

OTHER PUBLICATIONS

Tsuzuki et al., "Synthesis of CaC03 nanoparticles by mechanochemical processing." Journal of Nanoparticle Research, vol. 2, p. 375-380, 2000.
European Office Action in correspondence EP Application No. 10766519.2, dated Feb. 28, 2013, 7 pages.
European Office Action dated Jan. 18, 2013 from application No. 10766515.0, 5 pages.
European Office Action dated Feb. 28, 2013 from application No. 10766519.2, 7 pages.
European Office Action dated Nov. 16, 2012 from application No. 10766521.8, 5 pages.
European Office Action dated Dec. 7, 2012 from application No. 10766513.5, 3 pages.
European Search Report in EP Application No. 10766519.2, dated Dec. 21, 2012, 5 pages.
Extended European Search Report in EP Application No. 05821508.8-2112, dated Jul. 31, 2012, 5 pages.
Extended European Search Report in EP Application No. 10766518.4, dated Nov. 5, 2012, 7 pages.
International Search Report in International Application No. PCT/AU2010/000464, dated Jun. 25, 2010, 4 pages.
International Search Report in International Application No. PCT/AU2010/000466, dated Jun. 22, 2010, 4 pages.
International Search Report in International Application No. PCT/AU2010/000467, dated Aug. 12, 2010, 4 pages.
International Search Report in International Application No. PCT/AU2010/000468, dated Jun. 22, 2010, 4 pages.
International Search Report in International Application No. PCT/AU2010/000469, dated Jun. 17, 2010, 4 pages.
International Search Report in International Application No. PCT/AU2010/000471, dated Jun. 17, 2010, 3 pages.
International Search Report in International Application No. PCT/AU2010/000472, dated Jun. 22, 2010, 3 pages.
Office Action in corresponding Indonesia Patent Application No. HKI-3-HI.05.01.04.4248, dated Jun. 24, 2013, 4 pages.
Aoki et al., "Premedication with cyclooxygenase-2 inhibitor meloxicam reduced postoperative pain in patients after oral surgery," Abstract Only—International Journal of Oral and Maxillofacial Surgery, 35(7):613-617 (2006).
Narjes et al., "Pharmacokinetics and tolerability of meloxicam after i.m. administration," British Journal of Clinical Pharmacology, 41(2):135-139 (1996).
International Search Report and Written Opinion of corresponding Application No. PCT/US2015/034923, dated Sep. 1, 2015, pp. 1-12.
International Preliminary Report on Patentability in International Application No. PCT/US2015/034923, dated Dec. 22, 2016, 11 pages.

FORMULATION OF MELOXICAM

RELATED APPLICATIONS

This application is a continuation and claims priority to U.S. patent application Ser. No. 14/974,108, filed on Dec. 18, 2015, which is a continuation and claims priority to U.S. patent application Ser. No. 14/675,410, filed on Mar. 31, 2015, which claims priority under 35 USC §119(e) to provisional U.S. Patent Application 62/009,860, filed on Jun. 9, 2014, the entire contents of which is hereby incorporated by reference.

FIELD OF THE DISCLOSURE

The present disclosure relates to compositions comprising meloxicam, medicaments produced using meloxicam in particulate form and to methods of treatment of an animal, including man, using a therapeutically effective amount of meloxicam administered by way of such medicaments. Also described are methods for producing particles of meloxicam using dry milling processes and processes for producing medicaments by further processing material produced by dry milling.

BACKGROUND

Nonsteroidal anti-inflammatory drugs (NSAIDs) are widely used to treat acute and chronic pain, inflammation, and fever. Some of the active agents in this class include aspirin, ibuprofen, naproxen, diclofenac, indomethacin, celecoxib, and meloxicam. Meloxicam was first approved for marketing in the U.S. in 2000 under the trade name Mobic® (Boehringer Ingelheim). It is available as oral tablets (7.5 mg and 15 mg potencies) and as an oral suspension (7.5 mg/5 mL). Mobic is indicated for the treatment of osteoarthritis, rheumatoid arthritis, and juvenile rheumatoid arthritis. The recommend starting and maintenance dose is 7.5 mg per day. The maximum recommended daily dose is 15 mg per day. While NSAIDs have significant analgesic, anti-inflammatory, and antipyretic activity, they are also associated with serious dose-related side effects such as gastrointestinal perforation and bleeding, cardiovascular events including myocardial infarction, and renal failure. As a result, all FDA-approved NSAID products marketed in the United States, including meloxicam contain labeling statements instructing prescribing physicians to use the lowest effective dose for the shortest possible duration. Thus, it is desirable to provide therapeutically effective NSAID products with drug doses that are lower than those currently available to patients suffering from acute or chronic pain.

Meloxicam is a member of the enolic acid group of NSAIDs and is chemically designated as 4-hydroxy-2-methyl-N-(5-methyl-2-thiazolyl)-2H-1,2-benzothiazine-3-carboxamide-1,1-dioxide. It is practically insoluble in water. Poor solubility is a significant problem encountered in the development of compositions for the pharmaceutical, cosmetic, agricultural and food industries, particularly those compositions containing a biologically active material that is poorly soluble in water at physiological pH. In many instances, poorly soluble compounds have undesirable pharmacokinetic properties such as slow dissolution and slow or incomplete oral absorption from the gastrointestinal tract to the systemic circulation. In addition, poorly soluble active agents tend to be disfavored or even unsafe for intravenous administration due to the risk of particles of agent blocking blood flow through capillaries.

It is known that the rate of dissolution of a particulate drug will increase with increasing surface area. One way of increasing surface area is decreasing particle size. Consequently, methods of making finely divided or sized drugs have been studied with a view to controlling the size and size range of drug particles for pharmaceutical compositions.

SUMMARY

Described herein are unit dosage forms of meloxicam containing either 5 mg or 10 mg of meloxicam that provide effective pain relief and have desirable pharmacokinetic properties. The unit dosage forms can provide pain relief when a single unit dose is administered to a patient. The unit dosage forms are useful for treating pain such as osteoarthritis pain at a relatively low systemic exposure to meloxicam.

In some embodiments of the 5 mg unit dosage form described above, a single dose, upon oral administration to a population of healthy adults in the fasted state, provides a mean plasma AUC (0-∞) of 7500-20000 h*ng/ml; a single dose, upon oral administration to a population of healthy adults in the fasted state, provides a mean plasma Cmax of 400-900 ng/ml; a single dose, upon oral administration to a population of healthy adults in the fasted state, provides a median Tmax of 1-3 hours; a single dose, upon oral administration to a population of healthy adults in the fasted state, provides a mean plasma AUC (0-∞) that is 80% to 125% of 13610 ng-h/ml; a single dose, upon oral administration to a population of healthy adults in the fasted state, provides a mean plasma Cmax that is 80% to 125% of 642 ng/ml.

Described herein is a solid unit dosage form of a pharmaceutical composition comprising 5 mg of meloxicam and one or more pharmaceutically acceptable excipients, wherein the particles of meloxicam have a median particle size, on a volume average basis, between 100 nm and 5000 nm. In various cases: the D(0.9) of the particles of meloxicam is less than 3000 nm; the surface weighted mean diameter (D[3,2]) of the particles of meloxicam is between 100 nm and 800 nm; volume weighted mean diameter (D[4,3]) of the particles of meloxicam is between 400 nm and 1300 nm; the dissolution rate of the unit dosage from is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 80% of the meloxicam dissolves in a time period selected from: 30 minutes or less; 20 minutes or less; 10 minutes or less; and 5 minutes or less. In other cases the dissolution rate of the unit dosage form is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 90% of the meloxicam dissolves in a time period selected from: 30 minutes or less; 20 minutes or less; 10 minutes or less; and 5 minutes or less. In various cases: a single dose, upon oral administration to a population of healthy adults in the fasted state, provides a mean blood plasma AUC (0-∞) of 7500-20000 h*ng/ml; a single dose, upon oral administration to a population of healthy adults in the fasted state, provides a mean blood plasma Cmax of 400-900 ng/ml; a single dose, upon oral administration to a population of healthy adults in the fasted state, provides a mean blood plasma Cmax of 400-900 ng/ml; a single dose, upon oral administration to a population of healthy adults in the fasted state, provides a mean blood plasma AUC (0-∞) of 7500-

20000 h*ng/ml; a single dose, upon oral administration to a population of healthy adults in the fasted state, provides a mean blood plasma AUC (0-∞) that is 80% to 125% of 13610 ng-h/ml; a single dose, upon oral administration to a population of healthy adults in the fasted state, provides a mean blood plasma Cmax that is 80% to 125% of 642 ng/ml.

Also described herein is a solid unit dosage form of a pharmaceutical composition comprising 5 mg of meloxicam, wherein a single dose, upon oral administration to a population of healthy adults in the fasted state, provides a mean blood plasma Cmax of 350-950 ng/ml. Also described is a solid unit dosage form of a pharmaceutical composition comprising 5 mg of meloxicam, wherein a single dose, upon oral administration to a population of healthy adults in the fasted state, provides a mean blood plasma AUC (0-∞) of 7500-20000 h*ng/ml. In various cases of these dosage forms: the particles of meloxicam have a median particle size, on a volume average basis, between 100 nm and 5000 nm. In various cases: the D(0.9) of the particles of meloxicam is less than 3000 nm; the surface weighted mean diameter (D[3,2]) of the particles of meloxicam is between 100 nm and 800 nm; and volume weighted mean diameter (D[4,3]) of the particles of meloxicam is between 400 nm and 1300 nm.

In some embodiments of the 5 mg unit dosage form described above, the dissolution rate of the unit dosage form is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 80% of the meloxicam dissolves in a time period selected from: 30 minutes or less; 20 minutes or less; 10 minutes or less; and 5 minutes or less. In other cases the dissolution rate of the unit dosage form is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 90% of the meloxicam dissolves in a time period selected from: 30 minutes or less; 20 minutes or less; 10 minutes or less; and 5 minutes or less.

In some embodiments of the 5 mg unit dosage form: the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 90% of the meloxicam dissolves in 30 minutes; at least 90% of the meloxicam dissolves in 20 minutes; at least 90% of the meloxicam dissolves in 10 minutes; at least 95% of the meloxicam dissolves in 30 minutes; at least 95% of the meloxicam dissolves in 20 minutes; at least 95% of the meloxicam dissolves in 10 minutes; at least 70% of the meloxicam dissolves in 5 minutes.

In some embodiments of the 5 mg unit dosage form: the mean Cmax of a single unit is within 80.00% to 125.00% of the mean Cmax of 7.5 mg Mobic tablets, when a single unit is administered to a population of healthy adults in the fasted state; a single unit, upon oral administration to a population of healthy adult patients in the fasted state, provides a mean blood plasma AUC (0-∞) hours that is 60%-80% of the mean blood plasma AUC (0-∞) hours of 7.5 mg Mobic tablets, when a single dose is administered to a population of healthy adults in the fasted state; the unit dosage form is a capsule or a tablet; the unit dosage form is a hard gelatin capsule.

In various cases: a single dose, upon oral administration to a population of healthy adults in the fasted state, provides a mean blood plasma AUC (0-∞) of 7500-20000 h*ng/ml; a single dose, upon oral administration to a population of healthy adults in the fasted state, provides a mean blood plasma Cmax of 400-900 ng/ml; a single dose, upon oral administration to a population of healthy adults in the fasted state, provides a mean blood plasma Cmax of 400-900 ng/ml; a single dose, upon oral administration to a population of healthy adults in the fasted state, provides a mean blood plasma AUC (0-∞) of 7500-20000 h*ng/ml; a single dose, upon oral administration to a population of healthy adults in the fasted state, provides a mean blood plasma AUC (0-∞) that is 80% to 125% of 13610 ng-h/ml; a single dose, upon oral administration to a population of healthy adults in the fasted state, provides a mean blood plasma Cmax that is 80% to 125% of 642 ng/ml.

Also described herein is a unit dosage form comprising 10 mg of meloxicam. In some embodiments, a single dose, upon oral administration to a population of healthy adults in the fasted state, provides a mean plasma AUC (0-∞) of 16000-44000 h*ng/ml; a single dose, upon oral administration to a population of healthy adults in the fasted state, provides a mean plasma Cmax of 850-1750 ng/ml; a single dose, upon oral administration to a population of healthy adults in the fasted state, provides a median plasma Tmax of 1 to 3 hrs; a single dose, upon oral administration to a population of healthy adults in the fasted state, provides a mean plasma AUC (0-∞) that is 80% to 125% of 29,173 ng-h/ml; a single dose, upon oral administration to a population of healthy adults in the fasted state, provides a mean plasma Cmax that is 80% to 125% of 1253 ng/ml.

In some embodiments, the dissolution rate of the 10 mg unit dosage form is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 80% of the meloxicam dissolves in a time period selected from: 30 minutes or less; 20 minutes or less; 10 minutes or less; and 5 minutes or less; the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 90% of the meloxicam dissolves in a time period selected from: 30 minutes or less; 20 minutes or less; 10 minutes or less; and 5 minutes or less. and one or more pharmaceutically acceptable excipients, wherein the particles of meloxicam have a median particle size, on a volume average basis, between 100 nm and 5000 nm. In various cases: the D(0.9) of the particles of meloxicam is less than 3000 nm; the surface weighted mean diameter (D[3,2]) of the particles of meloxicam is between 100 nm and 800 nm; the volume weighted mean diameter (D[4,3]) of the particles of meloxicam is between 400 nm and 1300 nm; the dissolution rate of the unit dosage form is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 80% of the meloxicam dissolves in a time period selected from: 30 minutes or less; 20 minutes or less; 10 minutes or less; and 5 minutes or less; the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 90% of the meloxicam dissolves in a time period selected from: 30 minutes or less; 20 minutes or less; 10 minutes or less; and 5 minutes or less; a single dose, upon oral administration to a population of healthy adults in the fasted state, provides a median blood plasma tmax of 1 to 3 hrs; a single dose, upon oral administration to a population of healthy adults in the fasted state, provides a mean blood plasma AUC (0-∞) of 16000-44000 h*ng/ml; a single dose, upon oral administration to a population of healthy adults in the fasted state, provides a mean blood plasma Cmax of 850-1750 ng/ml; a single dose, upon oral administration to a population of healthy adults in the fasted state, provides a mean blood plasma AUC (0-∞) that is 80% to 125% of 29,173 ng-h/ml; a single dose, upon oral administration to a population of healthy adults in the fasted state, provides a mean blood plasma Cmax that is 80% to 125% of 1253 ng/ml.

Also described herein is a solid unit dosage form of a pharmaceutical composition comprising 10 mg of meloxicam and one or more pharmaceutically acceptable excipients wherein a single dose, upon oral administration to a population of healthy adults in the fasted state, provides a mean blood plasma AUC (0-∞) of 16000-44000 h*ng/ml. Also described herein is a unit dosage form of a pharmaceutical composition comprising 10 mg of meloxicam and one or more pharmaceutically acceptable excipients wherein a single dose, a single dose, upon oral administration to a population of healthy adults in the fasted state, provides a mean blood plasma Cmax of 850-1750 ng/ml. In various embodiments: the particles of meloxicam have a median particle size, on a volume average basis, between 100 nm and 5000 nm. In various cases: the D(0.9) of the particles of meloxicam is less than 3000 nm; the surface weighted mean diameter (D[3,2]) of the particles of meloxicam is between 100 nm and 800 nm; the volume weighted mean diameter (D[4,3]) of the particles of meloxicam is between 400 nm and 1300 nm; the dissolution rate of the unit dosage form is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 80% of the meloxicam dissolves in a time period selected from: 30 minutes or less; 20 minutes or less; 10 minutes or less; and 5 minutes or less; the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 90% of the meloxicam dissolves in a time period selected from: 30 minutes or less; 20 minutes or less; 10 minutes or less; and 5 minutes or less; a single dose, upon oral administration to a population of healthy adults in the fasted state, provides a median blood plasma tmax of 1 to 3 hrs; a single dose, upon oral administration to a population of healthy adults in the fasted state, provides a mean blood plasma AUC (0-∞) that is 80% to 125% of 29,173 ng-h/ml; a single dose, upon oral administration to a population of healthy adults in the fasted state, provides a mean blood plasma Cmax that is 80% to 125% of 1253 ng/ml.

In the case of the solid unit dosage forms containing 10 mg of meloxicam, in some embodiments: a single dose, upon oral administration to a population of healthy adults in the fed state, provides a mean blood plasma Cmax of 525-1500 ng/ml; a single dose, upon oral administration to a population of healthy adults in the fed state, provides a median blood plasma tmax of 3 to 7 hrs; a single dose, upon oral administration to a population healthy adults in the fed state, provides a mean blood plasma AUC (0-∞) of 15000-42000 h*ng/ml; a single dose, upon oral administration to a population of healthy adults in the fed state, provides a mean blood plasma Cmax that is 80% to 125% of 27,146 ng/ml.

In some embodiments of the 5 mg and 10 mg unit dosage forms described above the particles of meloxicam have a median particle size, determined on a particle volume basis, that is greater than 100 nm and is equal or less than a size selected from the group consisting of 5000 nm, 4500 nm, 4000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, and 200 nm In some embodiments, the D90 of the particle size distribution, as measured on a particle volume basis, is selected from the group consisting of less than or equal, 4000 nm, 3000 nm, 2000 nm, 1900 nm, 1800 nm, 1700 nm, 1600 nm, 1500 nm, 1400 nm, 1300 nm, 1200 nm, 1100 nm, or 1000 nm and, in some cases, greater than 900 nm.

In some embodiments of the 5 mg unit dosage form: the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 90% of the meloxicam dissolves in 30 minutes; the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 90% of the meloxicam dissolves in 20 minutes; the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 90% of the meloxicam dissolves in 10 minutes; the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 95% of the meloxicam dissolves in 30 minutes; the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 95% of the meloxicam dissolves in 20 minutes; the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 95% of the meloxicam dissolves in 10 minutes; the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 70% of the meloxicam dissolves in 5 minutes;

In some embodiments of the 5 mg unit dosage form: the 90% CI of the mean Cmax of a single unit is within 80.00% to 125.00% of the mean Cmax of 7.5 mg Mobic tablets, when a single unit is administered to an adult in the fasted state; a single unit, upon oral administration to an adult patient in the fasted state, provides a mean blood plasma AUC (0-48) hours that is 70%-85% of the mean blood plasma AUC (0-48) hours of 7.5 mg Mobic tablets, when a single dose is administered to an adult in the fasted state; the unit dosage from is a capsule or a tablet; the unit dosage form is a hard gelatin capsule.

In some embodiments of the 10 mg dosage form: the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 90% of the meloxicam dissolves in 30 minutes; the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 90% of the meloxicam dissolves in 20 minutes; the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 90% of the meloxicam dissolves in 10 minutes; the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 95% of the meloxicam dissolves in 30 minutes; the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 95% of the meloxicam dissolves in 20 minutes; the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 95% of the meloxicam dissolves in 10 minutes; the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 70% of the meloxicam dissolves in 5 minutes; the 90% CI of the mean Cmax is with 80.00% to 125.00% of the mean Cmax of 15 mg Mobic tablets, when a single unit is administered to a population of healthy adults in the fasted state; a single unit, upon oral administration to a population of healthy adults in the fasted state, provides a mean blood plasma AUC (0-∞) hours that is 60%-80% of the mean blood plasma AUC (0-∞) hours of 15 mg Mobic tablets, when a single unit is administered to a population of healthy adults in the fasted state; the unit dosage form is a capsule or a tablet; the unit dosage form is a hard gelatin capsule.

In some embodiments of the 5 mg and 10 mg unit dosage forms described above the particles of meloxicam have a median particle size, determined on a particle volume basis, that is greater than 100 nm and is equal or less than a size selected from the group consisting of 5000 nm, 4500 nm, 4000 nm, 3000 nm, 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, and 200 nm. In some embodiments, the D90 of the particle size distribution, as measured on a particle volume basis, is selected from the group consisting of less than or equal, 4000 nm, 3000 nm, 2000 nm, 1900 nm, 1800 nm, 1700 nm, 1600 nm, 1500 nm, 1400 nm, 1300 nm, 1200 nm, 1100 nm, or 1000 nm and, in some cases, greater than 900 nm. In some embodiments the surface weighted mean diameter (D[3,2]) of the particles of meloxicam is between 100 nm and 800 nm; in some embodiments the volume weighted mean diameter (D[4,3]) of the particles of meloxicam is between 400 nm and 1300 nm.

Pharmacokinetic testing in human subjects demonstrated that single doses of the 5 mg and 10 mg unit dosages of the present invention were more rapidly absorbed than a 15 mg dosage of Mobic when all test articles were taken in the fasted state. The median time to maximum plasma concentration (Tmax) for the 5 mg and 10 mg dosages was 2 hours, while the median time to Tmax for the 15 mg Mobic tablet was 4 hours. The testing also demonstrated that a single dose of the 10 mg unit dosage form exhibited about ⅓ lower systemic exposure (AUC) compared to a single dose of a conventional 15 mg Mobic® tablet. Based on the dose-proportionality of the 10 mg and 5 mg dosage forms described herein, it is expected that the 5 mg dosage form will exhibit about ⅓ lower systemic exposure compared to conventional 7.5 mg Mobic® tablets. Despite the lower systemic exposure observed for a single dose of the 10 mg dosage form compared to a single dose of the conventional 15 mg Mobic® tablet, the peak plasma concentration (Cmax) observed for a single dose of the 10 mg dosage form was comparable to that of a single dose of the conventional 15 mg Mobic® tablet.

The unit dosage forms described herein can be used to treat pain, e.g., pain associated with arthritis, e.g, osteoarthritis or rheumatoid arthritis. In some embodiments, the unit dosage is a solid dosage form. In some embodiments, the unit dosage comprises 5 mg or 10 mg of meloxicam and one or more pharmaceutically acceptable excipients.

The 5 mg unit dosage form can be administered 1 to 5 times daily with a single unit each time for a total dose of 5 mg for each administration. Alternatively, two units of the 5 mg unit dosage form can be administered 1 to 5 times daily with a single unit each time for a total dose of 5 mg for each administration.

The 10 mg unit dosage form can be administered 1 to 5 times daily with a single unit each time for a total dose of 10 mg for each administration.

In some cases, the crystallinity profile of the meloxicam in the dosage form is selected from the group consisting of: at least 20% of the biologically active material is crystalline, at least 30% of the biologically active material is crystalline, at least 40% of the biologically active material is crystalline, at least 50% of the biologically active material is crystalline, at least 60% of the biologically active material is crystalline, at least 70% of the biologically active material is crystalline, at least 75% of the biologically active material is crystalline, at least 85% of the biologically active material is crystalline, at least 90% of the biologically active material is crystalline, at least 95% of the biologically active material is crystalline and at least 98% of the biologically active material is crystalline. In some cases, the crystallinity profile of the biologically active material is substantially equal to the crystallinity profile of the biologically active material before the material was subjected to the method as described herein.

The disclosure also includes methods for dry milling meloxicam in presence of a plurality of milling bodies, a millable grinding matrix, and a facilitating agent, e.g., a surfactant.

In some embodiments, the milling time period is a range selected from the group consisting of: between 10 minutes and 3 hours, between 10 minutes and 2.5 hours, between 10 minutes and w hours, between, between 20 minutes and 2 hours, between 20 minutes and 90 minutes, and between 30 minutes and 90 minutes.

In some embodiments, the milling bodies are formed of a material is selected from the group consisting of: ceramics, glasses, polymers, ferromagnetics and metals. In some cases, the milling bodies are steel balls having a diameter selected from the group consisting of: between 1 and 20 mm, between 2 and 15 mm and between 3 and 10 mm. In some cases, the milling bodies are zirconium oxide balls having a diameter selected from the group consisting of: between 1 and 20 mm, between 2 and 15 mm and between 3 and 10 mm. In some embodiments, the dry milling apparatus is a mill selected from the group consisting of: attritor mills (horizontal or vertical), nutating mills, tower mills, pearl mills, planetary mills, vibratory mills, eccentric vibratory mills, gravity-dependent-type ball mills, rod mills, roller mills and crusher mills. In some cases, the milling bodies within the milling apparatus are mechanically agitated by 1, 2 or 3 rotating shafts. In some cases, the method is configured to produce the biologically active material in a continuous fashion.

In some cases, the total combined amount of biologically active material and grinding matrix in the mill at any given time is equal to or greater than a mass selected from the group consisting of: 200 grams, 500 grams, 1 kg, 2 kg, 5 kg, 10 kg, 20 kg, 30 kg, 50 kg, 75 kg, 100 kg, 150 kg, and 200 kg. Preferably, the total combined amount of biologically active material and grinding matrix is less than 2000 kg.

In some embodiments the millable grinding matrix is selected from the group consisting of: mannitol, sorbitol, Isomalt, xylitol, maltitol, lactitol, erythritol, arabitol, ribitol, glucose, fructose, mannose, galactose, anhydrous lactose, lactose monohydrate, sucrose, maltose, trehalose, maltodextrins, dextrin, Inulin, dextrates, polydextrose, starch, wheat flour, corn flour, rice flour, rice starch, tapioca flour, tapioca starch, potato flour, potato starch, other flours and starches, milk powder, skim milk powders, other milk solids and derivatives, soy flour, soy meal or other soy products, cellulose, microcystalline cellulose, microcystalline cellulose based co-blended materials, pregelatinized (or partially) starch, HPMC, CMC, HPC, citric acid, tartaric acid, malic acid, maleic acid fumaric acid, ascorbic acid, succinic acid, sodium citrate, sodium tartrate, sodium malate, sodium ascorbate, potassium citrate, potassium tartrate, potassium malate, sodium acetate, potassium ascorbate, sodium carbonate, potassium carbonate, magnesium carbonate, sodium bicarbonate, potassium bicarbonate, calcium carbonate, dibasic calcium phosphate, tribasic calcium phosphate, sodium sulfate, sodium chloride, sodium metabisulphite, sodium thiosulfate, ammonium chloride, glauber's salt, ammonium carbonate, sodium bisulfate, magnesium sulfate, potash alum, potassium chloride, sodium hydrogen sulfate, sodium hydroxide, crystalline hydroxides, hydrogen carbonates, ammonium chloride, methylamine hydrochloride, ammonium bromide, silica, thermal silica, alumina, titanium dioxide, talc, chalk, mica, kaolin, bentonite, hectorite, magnesium trisilicate, clay based materials or aluminium silicates, sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, sucrose palmitate, sucrose stearate, sucrose distearate, sucrose laurate, glycocholic acid, sodium glycolate, cholic acid, sodium cholate, sodium deoxycholate, deoxycholic acid, sodium taurocholate, taurocholic acid, sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, calcium dodecylbenzene sulfonate, sodium dodecylbenzene sulfonate, diisopropyl naphthaenesulphonate, erythritol distearate, naphthalene sulfonate formaldehyde condensate, nonylphenol ethoxylate (poe-30), tristyrylphenol ethoxylate, polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, sodium methyl naphthalene formaldehyde sulfonate, sodium n-butyl naphthalene sulfonate, tridecyl alcohol ethoxylate (poe-18), triethanolamine isodecanol phosphate ester, triethanolamine tristyrylphosphate ester, tristyrylphenol ethoxylate sulfate, bis(2-hydroxyethyl)tallowalkylamines or mixtures thereof. Preferably, the concentration of millable grinding matrix (or the total amount of the two or more millable grinding matrices) is selected from the group consisting of: 5-99% w/w, 10-95% w/w, 15-85% w/w, of 20-80% w/w, 25-75% w/w, 30-60% w/w, 40-50% w/w. Preferably, the concentration of the facilitating agent is selected from 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1% w/w, of 0.75-1.25% w/w, 0.75-1% and 1% w/w.

In some embodiments, the facilitating agent is selected from the group consisting of: sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, Sucrose Palmitate, Sucrose Stearate, Sucrose Distearate, Sucrose laurate, Glycocholic acid, sodium Glycholate, Cholic Acid, Sodium Cholate, Sodium Deoxycholate, Deoxycholic acid, Sodium taurocholate, taurocholic acid, Sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, Calcium Dodecylbenzene Sulfonate, Sodium Dodecylbenzene Sulfonate, Diisopropyl naphthaenesulphonate, erythritol distearate, Naphthalene Sulfonate Formaldehyde Condensate, nonylphenol ethoxylate (poe-30), Tristyrylphenol Ethoxylate, Polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, Sodium Methyl Naphthalene Formaldehyde Sulfonate, sodium n-butyl naphthalene sulfonate, tridecyl alcohol ethoxylate (poe-18), Triethanolamine isodecanol phosphate ester, Triethanolamine tristyrylphosphate ester, Tristyrylphenol Ethoxylate Sulfate, Bis(2-hydroxyethyl)tallowalkylamines.

In other embodiments: meloxicam is milled with lactose monohydrate and alkyl sulfates; meloxicam is milled with lactose monohydrate and sodium lauryl sulphate; meloxicam is milled with lactose monohydrate and sodium octadecyl sulphate; Meloxicam is milled with lactose monohydrate, alkyl sulfates and another surfactant or polymers; meloxicam is milled with lactose monohydrate, sodium lauryl sulfate and polyether sulfates; meloxicam is milled with lactose monohydrate, sodium lauryl sulfate and polyethylene glycol 40 stearate; meloxicam is milled with lactose monohydrate, sodium lauryl sulfate and polyethylene glycol 100 stearate; meloxicam is milled with lactose monohydrate, sodium lauryl sulfate and a poloxamer; meloxicam is milled with lactose monohydrate, sodium lauryl sulfate and poloxamer 407; meloxicam is milled with lactose monohydrate, sodium lauryl sulfate and poloxamer 338; meloxicam is milled with lactose monohydrate, sodium lauryl sulfate and poloxamer 188; meloxicam is milled with lactose monohydrate, sodium lauryl sulfate and a solid polyethylene glycol; meloxicam is milled with lactose monohydrate, sodium lauryl sulfate and polyethylene glycol 6000; meloxicam is milled with lactose monohydrate, sodium lauryl sulfate and polyethylene glycol 3000; meloxicam is milled with lactose monohydrate and polyether sulfates; meloxicam is milled with lactose monohydrate and polyethylene glycol 40 stearate; meloxicam is milled with lactose monohydrate and polyethylene glycol 100 stearate meloxicam is milled with lactose monohydrate and polyvinyl-pyrrolidine; meloxicam is milled with lactose monohydrate and polyvinyl-pyrrolidone with an approximate molecular weight of 30,000-40,000; meloxicam is milled with lactose monohydrate and alkyl sulfonates; meloxicam is milled with lactose monohydrate and docusate sodium; meloxicam is milled with lactose monohydrate and a surfactant; meloxicam is milled with lactose monohydrate and lecithin; meloxicam is milled with lactose monohydrate and sodium n-lauroyl sarcosine; meloxicam is milled with lactose monohydrate and polyoxyethylene alkyl ether surfactants; meloxicam is milled with lactose monohydrate and PEG 6000. In another preferred formulation meloxicam is milled with lactose monohydrate and silica; meloxicam is milled with lactose monohydrate and Aerosil R972 fumed silica; meloxicam is milled with lactose monohydrate, tartaric acid and sodium lauryl sulfate; meloxicam is milled with with lactose monohydrate, sodium bicarbonate and sodium lauryl sulfate; meloxicam is milled with lactose monohydrate, potassium bicarbonate and sodium lauryl sulfate. In another preferred embodiment, meloxicam is milled with mannitol and alkyl sulfates; meloxicam is milled with mannitol and sodium lauryl sulfate; meloxicam is milled with mannitol and sodium octadecyl sulfate; Meloxicam is milled with mannitol, alkyl sulfates and another surfactant or polymers; meloxicam is milled with mannitol, sodium lauryl sulfate and polyether sulfates; meloxicam is milled with mannitol, sodium lauryl sulfate and polyethylene glycol 40 stearate; meloxicam is milled with mannitol, sodium lauryl sulfate and polyethylene glycol 100 stearate; meloxicam is milled with mannitol, sodium lauryl sulfate and a poloxamer; meloxicam is milled with mannitol, sodium lauryl sulfate and poloxamer 407; meloxicam is milled with mannitol, sodium lauryl sulfate and poloxamer 338; meloxicam is milled with mannitol, sodium lauryl sulfate and poloxamer 188; meloxicam is milled with mannitol, sodium lauryl sulfate and a solid polyethylene glycol; meloxicam is milled with mannitol, sodium lauryl sulfate and polyethylene glycol 6000; meloxicam is milled with mannitol, sodium lauryl sulfate and polyethylene glycol 3000; Meloxicam is milled with mannitol and polyether sulfates; meloxicam is milled with mannitol and polyethylene glycol 40 stearate; meloxicam is milled with mannitol and polyethylene glycol 100 stearate In another preferred embodiment meloxicam is milled with mannitol and polyvinyl-pyrrolidine; meloxicam is milled with mannitol and polyvinyl-pyrrolidone with an approximate molecular weight of 30,000-40,000; meloxicam is milled with mannitol and alkyl sulfonates; meloxicam is milled with mannitol and docusate sodium; meloxicam is milled with mannitol and a surfactant; meloxicam is milled with mannitol and lecithin; meloxicam is milled with mannitol and sodium n-lauroyl sarcosine; meloxicam is milled with mannitol and polyoxyethylene alkyl ether surfactants; meloxicam is milled with mannitol and PEG 6000. In another preferred formulation meloxicam is milled with mannitol and silica; meloxicam is milled with mannitol and Aerosil R972 fumed silica; meloxicam is milled with mannitol, tartaric acid and sodium lauryl sulfate; meloxicam is milled with mannitol, sodium bicarbonate and sodium lauryl sulfate; and meloxicam is milled with mannitol, potassium bicarbonate and sodium lauryl sulfate.

Those skilled in the art will appreciate that the disclosure described herein is susceptible to variations and modifications other than those specifically described. It is to be understood that the disclosure includes all such variations and modifications. The disclosure also includes all of the steps, features, compositions and materials referred to or indicated in the specification, individually or collectively and any and all combinations or any two or more of the steps or features.

The present disclosure is not to be limited in scope by the specific embodiments described herein, which are intended for the purpose of exemplification only. Functionally equivalent products, compositions and methods are clearly within the scope of the disclosure as described herein.

The disclosure described herein may include one or more ranges of values (e.g. size, concentration etc). A range of values will be understood to include all values within the range, including the values defining the range, and values adjacent to the range that lead to the same or substantially the same outcome as the values immediately adjacent to that value which defines the boundary to the range.

The entire disclosures of all publications (including patents, patent applications, journal articles, laboratory manuals, books, or other documents) cited herein are hereby incorporated by reference. Inclusion does not constitute an admission is made that any of the references constitute prior art or are part of the common general knowledge of those working in the field to which this disclosure relates.

Throughout this specification, unless the context requires otherwise, the word "comprise" or variations, such as "comprises" or "comprising" will be understood to imply the inclusion of a stated integer, or group of integers, but not the exclusion of any other integers or group of integers. It is also noted that in this disclosure, and particularly in the claims and/or paragraphs, terms such as "comprises", "comprised", "comprising" and the like can have the meaning attributed to it in US Patent law; e.g., they can mean "includes", "included", "including", and the like.

"Therapeutically effective amount" as used herein with respect to methods of treatment and in particular drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

The term "inhibit" is defined to include its generally accepted meaning which includes prohibiting, preventing, restraining, and lowering, stopping, or reversing progression or severity, and such action on a resultant symptom. As such the present disclosure includes both medical therapeutic and prophylactic administration, as appropriate.

Particle Size

There is a wide range of techniques that can be utilized to characterize the particle size of a material. Those skilled in the art also understand that almost all these techniques do not physically measure the actually particle size, as one might measure something with a ruler, but measure a physical phenomenon which is interpreted to indicate a particle size.

For measurements made using a laser diffraction instrument, or an equivalent method known in the art, the term "median particle size" is defined as the median particle diameter as determined on an equivalent spherical particle volume basis. Where the term median is used, it is understood to describe the particle size that divides the population in half such that 50% of the population is greater than or less than this size. The median particle size is often written as D50, D(0.50) or D[0.5] or similar. As used herein D50, D(0.50) or D[0.5] or similar shall be taken to mean 'median particle size'.

The term "Dx of the particle size distribution" refers to the xth percentile of the distribution; thus, D90 refers to the 90th percentile, D95 refers to the 95th percentile, and so forth. Taking D90 as an example this can often be written as, D(0.90) or D[0.9] or similar. With respect to the median particle size and Dx an upper case D or lowercase d are interchangeable and have the same meaning. Another commonly used way of describing a particle size distribution measured by laser diffraction, or an equivalent method known in the art, is to describe what % of a distribution is under or over a nominated size. The term "percentage less than" also written as "%<" is defined as the percentage, by volume, of a particle size distribution under a nominated size—for example the %<1000 nm. The term "percentage greater than" also written as "%>" is defined as the percentage, by volume, of a particle size distribution over a nominated size—for example the %>1000 nm.

For many of the materials subject to the methods of this disclosure the particle size can be easily measured. Where the active material has poor water solubility and the matrix it is milled in has good water solubility the powder can simply be dispersed in an aqueous solvent. In this scenario the matrix dissolves leaving the active material dispersed in the solvent. This suspension can then be measured by techniques such as photon correlation spectroscopy or laser diffraction.

Suitable methods to measure an accurate particle size where the matrix has low solubility in a water-based dispersant are outlined below.

1. In the circumstance where an insoluble matrix such as microcrystalline cellulose prevents the measurement of the active material separation techniques such as filtration or centrifugation could be used to separate the insoluble matrix from the active material particles. Other ancillary techniques would also be required to determine if any active material was removed by the separation technique so that this could be taken into account.
2. In some circumstances image analysis could be used to obtain information about the particle size distribution of the active material. Suitable image measurement techniques might include transmission electron microscopy (TEM), scanning electron microscopy (SEM), optical microscopy and confocal microscopy. In addition to these standard techniques some additional technique would be required to be used in parallel to differentiate the active material and matrix particles. Depending on the chemical makeup of the materials involved possible techniques could be elemental analysis, Raman spectroscopy, FTIR spectroscopy or fluorescence spectroscopy.

Throughout this specification, unless the context requires otherwise, the phrase "dry mill" or variations, such as "dry milling", should be understood to refer to milling in at least the substantial absence of liquids. If liquids are present, they are present in such amounts that the contents of the mill retain the characteristics of a dry powder.

The term "millable" means that a material is capable of being reduced in particle under the dry milling conditions used. In some cases, the milled grinding matrix is of a comparable particle size to the biologically active material. In other cases the particle size of the matrix is substantially reduced by milling but the resulting particle size is larger than the milled biologically active material.

Grinding Matrix

As will be described subsequently, selection of an appropriate grinding matrix affords particular advantageous applications of the method of the present disclosure. Again, as will be described subsequently, a highly advantageous aspect of the present disclosure is that certain grinding matrixes appropriate for use in the method of the disclosure are also appropriate for use in a medicament. The present disclosure encompasses methods for the production of a medicament incorporating both meloxicam and the grinding matrix or in some cases the abiraterone acetate and a portion of the grinding matrix, medicaments so produced, and methods of treatment using the medicament. The medicament may include only the milled abiraterone acetate together with the milled grinding matrix or, more preferably, the milled meloxicam and milled grinding matrix may be combined with one or more pharmaceutically acceptable carriers, as well as any desired excipients or other like agents commonly used in the preparation of medicaments.

In some cases at least one component of the grinding matrix is harder than the meloxicam, and is thus capable of reducing the particle size of the meloxicam under the dry milling conditions of the disclosure. Again without wishing to be bound by theory, under these circumstances it is believed that the millable grinding matrix affords the advantage of the present disclosure through a second route, with the smaller particles of grinding matrix produced under the dry milling conditions enabling greater interaction with the meloxicam.

The quantity of the grinding matrix relative to the quantity of meloxicam, and the extent of size reduction of the grinding matrix, is sufficient to inhibit re-agglomeration of the particles of the active material. In some embodiments, the quantity of the grinding matrix relative to the quantity of meloxicam, and the extent of size reduction of the grinding matrix, is sufficient to inhibit re-agglomeration of the particles of the active material.

In some embodiments, the grinding matrix has a low tendency to agglomerate during dry milling. While it is difficult to objectively quantify the tendency to agglomerate during milling, it is possible to obtain a subjective measure by observing the level of "caking" of the grinding matrix in the milling chamber of the mill as dry milling progresses.

The grinding matrix may be an inorganic or organic substance.

Milling Bodies

In the method of the present disclosure, where milling bodies are utilized, the milling bodies are preferably chemically inert and rigid. The term "chemically-inert", as used herein, means that the milling bodies do not react chemically with the meloxicam or the grinding matrix.

As described above, the milling bodies are essentially resistant to fracture and erosion in the milling process.

The milling bodies are desirably provided in the form of bodies which may have any of a variety of smooth, regular shapes, flat or curved surfaces, and lacking sharp or raised edges. For example, suitable milling bodies can be in the form of bodies having ellipsoidal, ovoid, spherical or right cylindrical shapes. In some embodiments, the milling bodies are provided in the form of one or more of beads, balls, spheres, rods, right cylinders, drums or radius-end right cylinders (i.e., right cylinders having hemispherical bases with the same radius as the cylinder).

Depending on the nature of the meloxicam and the grinding matrix, the milling bodies desirably have an effective mean diameter between about 0.1 and 30 mm, more preferably between about 1 and about 15 mm, still more preferably between about 3 and 10 mm.

The milling bodies may comprise various substances such as ceramic, glass, metal or polymeric compositions, in a particulate form. Suitable metal milling bodies are typically spherical and generally have good hardness (i.e. RHC 60-70), roundness, high wear resistance, and narrow size distribution and can include, for example, balls fabricated from type 52100 chrome steel, type 304, 316 or 440C stainless steel or type 1065 high carbon steel.

Ceramics, for example, can be selected from a wide array of ceramics desirably having sufficient hardness and resistance to fracture to enable them to avoid being chipped or crushed during milling and also having sufficiently high density. Suitable densities for milling bodies can range from about 1 to 15 g/cm$^3$, preferably from about 1 to 8 g/cm$^3$. Ceramics can be selected from steatite, aluminum oxide, zirconium oxide, zirconia-silica, yttria-stabilized zirconium oxide, magnesia-stabilized zirconium oxide, silicon nitride, silicon carbide, cobalt-stabilized tungsten carbide, and the like, as well as mixtures thereof.

Glass milling bodies are spherical (e.g. beads), have a narrow size distribution, are durable, and include, for example, lead-free soda lime glass and borosilicate glass. Polymeric milling bodies are preferably substantially spherical and can be selected from a wide array of polymeric resins having sufficient hardness and friability to enable them to avoid being chipped or crushed during milling, abrasion-resistance to minimize attrition resulting in contamination of the product, and freedom from impurities such as metals, solvents, and residual monomers.

Milling bodies can be formed from polymeric resins. Polymeric resins, for example, can be selected from crosslinked polystyrenes, such as polystyrene crosslinked with divinylbenzene, styrene copolymers, polyacrylates such as polymethylmethacrylate, polycarbonates, polyacetals, vinyl chloride polymers and copolymers, polyurethanes, polyamides, high density polyethylenes, polypropylenes, and the like. The use of polymeric milling bodies to grind materials down to a very small particle size (as opposed to mechanochemical synthesis) is disclosed, for example, in U.S. Pat. Nos. 5,478,705 and 5,500,331. Polymeric resins typically can have densities ranging from about 0.8 to 3.0 g/cm$^3$. Higher density polymeric resins are generally preferred. Alternatively, the milling bodies can be composite bodies comprising dense core bodies having a polymeric resin adhered thereon. Core particles can be selected from substances known to be useful as milling bodies, for example, glass, alumina, zirconia silica, zirconium oxide, stainless steel, and the like. Core substances have densities greater than about 2.5 g/cm$^3$.

In one embodiment of the disclosure, the milling bodies are formed from a ferromagnetic substance, thereby facilitating removal of contaminants arising from wear of the milling bodies by the use of magnetic separation techniques.

Each type of milling body has its own advantages. For example, metals have the highest specific gravities, which increase grinding efficiency due to increased impact energy. Metal costs range from low to high, but metal contamination of final product can be an issue. Glasses are advantageous from the standpoint of low cost and the availability of small bead sizes as low as 0.004 mm. However, the specific gravity of glasses is lower than other bodies and significantly more milling time is required. Finally, ceramics are advantageous from the standpoint of low wear and contamination, ease of cleaning, and high hardness.

Dry Milling

In the dry milling process of the present disclosure, the meloxicam and grinding matrix, in the form of crystals, powders, or the like, are combined in suitable proportions with or without a plurality of milling bodies in a milling chamber that is mechanically agitated for a predetermined period of time at a predetermined intensity of agitation. Typically, a milling apparatus is used to impart motion to contents of the mill including any milling bodies by the external application of agitation, a stream of dry gas or other force, whereby various translational, rotational or inversion motions or combinations thereof are applied to the milling chamber and its contents, or by the internal application of agitation through a rotating shaft terminating in a blade, propeller, impeller or paddle or by a combination of both actions.

During milling, motion imparted to the milling bodies or gas flowing through the milling system can result in application of shearing forces as well as multiple impacts or collisions having significant intensity between the mill components, any milling bodies utilized and the particles of meloxicam and the grinding matrix. The nature and intensity of the forces applied by the milling bodies to the meloxicam and the grinding matrix is influenced by a wide variety of processing parameters including: the type of milling apparatus; the intensity of the forces generated, the kinematic aspects of the process; the size, density, shape, and composition of any milling bodies used; the weight ratio of the meloxicam and grinding matrix mixture to the milling bodies; the duration of milling; the physical properties of both the meloxicam and the grinding matrix; the atmosphere present during milling; and others.

Advantageously, the mill is capable of repeatedly or continuously applying mechanical compressive forces and shear stress to the meloxicam and the grinding matrix. Throughout the remainder of the specification reference will be made to dry milling being carried out by way of a ball mill. Examples of this type of mill are attritor mills, nutating mills, tower mills, planetary mills, vibratory mills, gravity-dependent-type ball mills, rod mills, roller mills or crusher mills, and pulverizing mills. It will be appreciated that dry milling in accordance with the method of the disclosure may also be achieved by any suitable milling method or means.

In some cases, the particle size of the meloxicam prior to dry milling according to the methods described herein is less than about 1000 μm, as determined by sieve analysis. If the particle size of the meloxicam is greater than about 1000 μm, then it is preferred that the particles of the meloxicam substrate be reduced in size to less than 1000 μm using another particle size reduction method prior to dry milling according to the methods described herein.

Agglomerates of Meloxicam after Processing

Agglomerates comprising particles of meloxicam having a particle size within the ranges specified herein, should be understood to fall within the scope of the present disclosure, regardless of whether the agglomerates exceed the ranges specified above.

Processing Time

In some embodiments, the meloxicam and the grinding matrix are dry milled for the shortest time necessary to minimize any possible contamination from the mill process and/or any milling bodies utilized. This time varies greatly, depending on the meloxicam and the grinding matrix, and may range from as short as 1 minute to several hours.

Suitable rates of agitation and total milling times are adjusted for the type and size of milling apparatus, the type and size of any milling media utilized, the weight ratio of the meloxicam and grinding matrix mixture to the plurality of milling bodies that may be utilized, the chemical and physical properties of the meloxicam and grinding matrix, and other parameters that may be optimized empirically.

In some embodiments, the grinding matrix (the materials milled together with meloxicam) is not separated from the meloxicam but is maintained with the meloxicam in the final product. In some embodiments the grinding matrix is considered to be Generally Regarded as Safe (GRAS) for pharmaceutical products.

In an alternative aspect, the grinding matrix is separated from the meloxicam. In one aspect, where the grinding matrix is not fully milled, the unmilled grinding matrix is separated from the meloxicam. In a further aspect, at least a portion of the milled grinding matrix is separated from the meloxicam.

Any portion of the grinding matrix may be removed, including but not limited to 10%, 25%, 50%, 75%, or substantially all of the grinding matrix.

In some embodiments of the disclosure, a significant portion of the milled grinding matrix may comprise particles of a size similar to and/or smaller than the particles comprising the meloxicam. Where the portion of the milled grinding matrix to be separated from the particles comprising the meloxicam comprises particles of a size similar to and/or smaller than the particles comprising the meloxicam, separation techniques based on size distribution are inapplicable. In these circumstances, the method of the present disclosure may involve separation of at least a portion of the milled grinding matrix from the meloxicam by techniques including, but not limited to, electrostatic separation, magnetic separation, centrifugation (density separation), hydrodynamic separation, and froth flotation. Advantageously, the step of removing at least a portion of the milled grinding matrix from the meloxicam may be performed through means such as selective dissolution, washing, or sublimation.

An advantageous aspect of the disclosure would be the use of grinding matrix that has two or more components where at least one component is water soluble and at least one component has low solubility in water. In this case washing can be used to remove the matrix component soluble in water leaving the meloxicam dispersed in the remaining matrix components. In a highly advantageous aspect of the disclosure the matrix with low solubility is a functional excipient.

A highly advantageous aspect of the present disclosure is that certain grinding matrixes appropriate for use in the method of the disclosure are also pharmaceutically acceptable and thus appropriate for use in a medicament. Where the method of the present disclosure does not involve complete separation of the grinding matrix from the meloxicam, the present disclosure encompasses methods for the production of a medicament incorporating both the meloxicam and at least a portion of the milled grinding matrix, medicaments so produced and methods of treatment of an animal, including man, using a therapeutically effective amount of said meloxicam by way of said medicaments.

Dosage Forms

The dosage forms of the present disclosure may include meloxicam, optionally together with the grinding matrix or at least a portion of the grinding matrix, with or without milling aids, facilitating agents, combined with one or more pharmaceutically acceptable carriers, as well as other agents commonly used in the preparation of pharmaceutically acceptable compositions.

As used herein "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral administration, intravenous, intraperitoneal, intramuscular, sublingual, pulmonary, transdermal or oral administration. Pharmaceutically acceptable carriers include sterile aqueous solutions or dispersions and sterile powders for the extemporaneous preparation of sterile injectable solutions or dispersion. The use of such media and agents for the manufacture of medicaments is well known in the art. Except insofar as any conventional media or agent is incompatible with the pharmaceutically acceptable material, use thereof in the manufacture of a pharmaceutical composition according to the disclosure is contemplated.

Pharmaceutically acceptable carriers according to the disclosure may include one or more of the following examples:

(1) surfactants and polymers including, but not limited to polyethylene glycol (PEG), polyvinylpyrrolidone (PVP), polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropylmethyl cellulose phthalate, polyacrylates and polymethacrylates, urea, sugars, polyols, and their polymers, emulsifiers, sugar gum, starch, organic acids and their salts, vinyl pyrrolidone and vinyl acetate (2) binding agents such as various celluloses and cross-linked polyvinylpyrrolidone, microcrystalline cellulose; and or (3) filling agents such as lactose monohydrate, lactose anhydrous, microcrystalline cellulose and various starches; and or (4) lubricating agents such as agents that act on the flowability of the powder to be compressed, including colloidal silicon dioxide, talc, stearic acid, magnesium stearate, calcium stearate, silica gel; and or (5) sweeteners such as any natural or artificial sweetener including sucrose, xylitol, sodium saccharin, cyclamate, aspartame, and acesulfame K; and or (6) flavouring agents; and or (7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quaternary compounds such as benzalkonium chloride; and or (8) buffers; and or
(9) Diluents such as pharmaceutically acceptable inert fillers, such as microcrystalline cellulose, lactose, dibasic calcium phosphate, saccharides, and/or mixtures of any of the foregoing; and or
(10) wetting agents such as corn starch, potato starch, maize starch, and modified starches, croscarmellose sodium, crospovidone, sodium starch glycolate, and mixtures thereof; and or
(11) disintegrants; and or
(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and or
(13) other pharmaceutically acceptable excipients.

EXAMPLES

The following Examples are provided for illustrative purposes only, and are not intended to limit the scope of the processes or compositions of the disclosure.

Example 1: Production of Attrited Blends Containing Meloxicam

Meloxicam was dry milled in a mill with milling bodies in the presence of lactose monohydrate and sodium lauryl sulfate to produced attrited blends. In the attrited blends the particle size of the meloxicam is reduced compared to the starting material. Among the attrited blends produced in this manner were the two described below in Table 1.

TABLE 1

Composition of Two Attrited Blends

| Component | Attrited Blend 1 (% w/w) | Attrited Blend 2 (% w/w) |
|---|---|---|
| Meloxicam | 18.00 | 7.14 |
| Lactose monohydrate | 74.44 | 89.86 |
| Sodium lauryl sulfate | 7.56 | 3.00 |

The particle size distribution (PSD) of material in attrited blends can be determined using a Malvern Mastersizer 2000 fitted with a Malvern Hydro 2000S pump unit. Measurement settings can be: Measurement Time: 12 seconds, Measurement cycles: 3. Final result generated by averaging the 3 measurements. Samples can prepared by adding 200 mg of milled material to 5.0 mL of 1% PVP in 10 mM hydrochloric acid (HCl), vortexing for 1 min and then sonicating. From this suspension enough is added into the dispersant (10 mM HCl) to attain a desired obscuration level. If necessary an extra 1-2 minutes of sonication is applied using the internal sonication probe in the measurement cell. The refractive index of the active ingredient to be measured was in the range of 1.49-1.73. The particle size of meloxicam in two different attrited blends, both prepared in a manner similar to that used to prepare the attrited blends described above, was measured essentially as described above. The following values were obtained:

Attrited Blend A
Specific Surface Area: 31.8 m$^2$/g
Surface Weighted Mean D[3,2]: 0.189 μm
Volume Weighted Mean D[4,3]: 0.707 μm
D(10) or D(0.1): 0.082 μm
D(50) or D(0.5): 0.260 μm
D(90) or D(0.5): 1.945 μm
D(98) or D(0.98): 3.553 μm Attrited Blend B
Specific Surface Area: 33 m$^2$/g
Surface Weighted Mean D[3,2]: 0.182 μm
Volume Weighted Mean D[4,3]: 0.638 μm
D(10) or D(0.1): 0.081 μm
D(50) or D(0.5): 0.242 μm
D(90) or D(0.5): 1.768 μm
D(98) or D(0.98): 3.327 μm

Example 2: Preparation of Dosage Forms

The Attrited Blends were combined with intragranular excipients (microcrystalline cellulose, croscarmellose sodium, and sodium lauryl sulfate) and roller compacted into ribbons. The ribbons were milled into granules and blended with extragranular excipients (croscarmellose sodium, sodium lauryl sulfate, and sodium stearyl fumarate) to produce a Final Blend suitable for high speed automated encapsulation. The Final Blend was encapsulated to produce compositions containing 5 mg or 10 mg of meloxicam. The components of the Final Blend are as shown below in Table 2.

TABLE 2

Components of Final Blend for Preparation of Capsules

| Components | Final Blend (% w/w) |
|---|---|
| Meloxicam | 4.00 |
| Lactose monohydrate | 16.54 |
| Sodium lauryl sulfate | 1.68 |
| Microcrystalline cellulose - intragranular | 69.78 |
| Croscarmellose sodium - intragranular | 3.00 |
| Sodium lauryl sulfate - intragranular | 0.50 |
| Sodium stearyl fumarate - intragranular | 1.00 |
| Croscarmellose sodium - extragranular | 3.00 |
| Sodium lauryl sulfate - extragranular | 0.50 |
| Total | 100.0 |

The dissolution rate of meloxicam 5 mg and 10 mg capsules was analyzed. For the 5 mg capsules, the dissolution conditions were: USP Apparatus 1 (baskets) set to rotation speed of 100 RPM in 500 mL of pH 6.1 phosphate buffer with 0.1% sodium lauryl sulfate (SLS) at 37° C.±0.5° C. For the 10 mg capsules, the dissolution conditions were: USP Apparatus 1 (baskets) set to rotation speed of 100 RPM in 1000 mL of pH 6.1 phosphate buffer with 0.1% sodium lauryl sulfate (SLS) at 37° C.±0.5° C. For the 5 mg capsules, at least 90% of the meloxicam dissolved within 5 minutes. For the 10 mg capsules, at least 90% of the meloxicam dissolved within 10 minutes.

Example 3: Pharmacokinetic Testing

A human clinical trial was used to obtain pharmacokinetic data for the meloxicam 5 mg and 10 mg meloxicam capsules described above. Also tested was Mobic® 15 mg tablets. The results are presented in Table 3.

TABLE 3

Summary of Plasma Pharmacokinetic Parameters

| Parameter (unit) | Mean ± SD (N) | | | |
|---|---|---|---|---|
| | Meloxicam Capsules 10 mg (Fasted) | Meloxicam Capsules 10 mg (Fed) | Meloxicam Capsules 5 mg (Fasted) | Mobic 15 mg Tablet (Fasted) |
| $C_{max}$ (ng/mL) | 1252.78 ± 254.22 (27) | 973.88 ± 165.36 (26) | 642.39 ± 138.49 (26) | 1288.81 ± 424.40 (27) |
| $t_{max}$* (h) | 2.00 (1.00, 5.00) (27) | 5.00 (1.50, 16.02) (26) | 2.00 (0.50, 4.07) (26) | 4.00 (2.02, 8.00) (27) |
| $AUC_{0-t}$ (ng * h/mL) | 28190.52 ± 9264.72 (27) | 26681.19 ± 9748.03 (26) | 14206.47 ± 5415.31 (26) | 39093.82 ± 16500.17 (27) |
| $AUC_{0-\infty}$ (ng * h/mL) | 29173.01 ± 11042.09 (26) | 27145.85 ± 11469.51 (24) | 13610.54 ± 3342.69 (26) | 40875.58 ± 11733.47 (23) |
| $t_{1/2}$ (h) | 22.04 ± 10.08 (27) | 22.27 ± 9.88 (26) | 22.32 ± 10.91 (26) | 23.64 ± 10.04 (27) |

N = number of subjects randomized
*$t_{max}$ is presented as median (min, max)

Example 4: Clinical Testing in Patients Suffering Osteoarthritis (OA)-Related Pain A Phase 3, multicenter, randomized, double-blind, double-dummy, placebo-controlled, fixed-dose, parallel-group trial that included 403 subjects with clinical and radiologic evidence of osteoarthritis (OA)-related pain that required NSAID or acetaminophen treatment.

The subject population was representative of patients with active OA requiring acetaminophen or NSAID treatment—the mean age overall was 60.7 years, and subjects were generally overweight (mean BMI, 30.94 kg/m²).

Assessments of OA-associated pain and measures of function and stiffness utilized the WOMAC scale, a standard instrument that has been widely used to evaluate the utility of pharmacologic and non-pharmacologic interventions for the treatment of OA. Additional measures included pain intensity assessed by an 11-point numerical pain scale prior to and 2 hours after dosing and patient and clinical global impressions of change at Week 12.

WOMAC pain subscale scores at Baseline prior to randomization were high, indicative of a high degree of OA pain in the trial subjects, and were similar across treatment groups; the mean overall score (72.64 mm) was nearly twice the required minimum score for trial entry (40 mm).

Efficacy of Meloxicam Capsules 5 mg and 10 mg prepared as described herein was demonstrated by a combination of clinically meaningful and statistically significant results in the primary, secondary, and post hoc analyses. The primary efficacy parameter, change from Baseline to Week 12 in the WOMAC pain subscale score (MMRM analysis), demonstrated a statistically significant treatment benefit for once daily Meloxicam Capsules at both 5 mg (P=0.0005) and 10 mg (P=0.0059) dose levels compared with placebo.

Sensitivity analyses, which included more conservative requirements to establish efficacy, demonstrated that the model used in this analysis was robust and reliable. As a whole, although the limited numbers (resulting from low dropout rates) made it difficult to adequately assess the missing data mechanism, it was concluded that the primary efficacy analyses were appropriate and that the missing at random (MAR) assumption required to use the MMRM model assumptions appear reasonable.

Sensitivity analyses assessing the effect of rescue medication usage were also consistent with the primary efficacy analysis. The Silverman Integrated Rank Analysis, which takes into account rescue medication use and WOMAC pain subscale scores simultaneously, demonstrated a statistically significant difference in the LS mean change from Baseline to Week 12 for both the Meloxicam Capsules 5 mg (P<0.0001) and 10 mg (P<0.0001) groups compared with placebo.

Secondary efficacy analyses of WOMAC pain subscale scores confirmed the results of the primary efficacy analysis. Treatment with Meloxicam Capsules 5 mg once daily resulted in significant changes from Baseline in WOMAC pain subscale scores at Weeks 2 (P=0.0003) and 6 (P=0.0004), and for the average of the 12-week trial period (P<0.0001), compared with placebo. Evidence of efficacy was also noted for the Meloxicam Capsules 10 mg treatment group at each trial visit; significant improvements compared with placebo were observed for the change from Baseline to Week 6 (P=0.0008) and to the average over the 12-week period (P=0.0024).

Similar to the results based on the WOMAC pain subscale, significant differences vs placebo in the LS mean change from Baseline in WOMAC function subscale scores were achieved by the Meloxicam Capsules 5 mg group at Week 2 (P=0.0001), Week 6 (P=0.0012), Week 12 (P=0.0014), and for the average over the 12-week period (P<0.0001). Significant differences vs placebo were also noted for the Meloxicam Capsules 10 mg treatment at Weeks 6 (P=0.0014), Week 12 (P=0.0014), and for the average over the 12-week period (P=0.0018). Significant differences in WOMAC stiffness subscale scores were achieved by both the Meloxicam Capsules 5 mg and 10 mg groups for Weeks 2, 6, 12, and the average over the 12-week period (5 mg: P≤0.0001, 10 mg: P≤0.0379). These results demonstrate that both dosing regimens of Meloxicam Capsules not only provide relief of pain associated with OA, but also improve functional deficits and stiffness associated with OA.

The total WOMAC score provides a useful measure of improvement in overall symptoms associated with OA, including function, stiffness, and pain. Subjects in the Meloxicam Capsules 5 mg and 10 mg treatment groups achieved lower mean scores at each post-Baseline trial visit compared with the placebo group. Significant differences vs placebo in the LS mean change from Baseline in total WOMAC scores were achieved by the Meloxicam Capsules 5 mg group at each trial visit and over the 12-week period (P≤0.0014). Significant differences vs placebo were also noted for the Meloxicam Capsules 10 mg treatment group at Week 6, Week 12, and the average over the 12-week trial period (P≤0.0020).

Significant numbers of subjects in the Meloxicam Capsules 5 mg group were considered responders to trial drug treatment based on minimal differences in WOMAC pain subscale scores (10 mm) from Baseline at Weeks 2 and 6 and clinically meaningful (ie, ≥30% and ≥50%) reductions in WOMAC pain subscale scores from Baseline at Weeks 2, 6, and 12 following the start of dosing compared with placebo. A higher number of subjects in the Meloxicam Capsules 5 mg group also achieved ≥10 mm reduction in WOMAC pain subscale scores from Baseline at Week 12. Significant numbers of subjects in the Meloxicam Capsules 10 mg group were considered responders at Weeks 6 (≥10 mm, ≥30%, ≥50% reductions in WOMAC pain subscale) and 12 (≥50% reduction in WOMAC pain subscale) compared with placebo. Significantly more responders were noted in the Meloxicam Capsules 5 mg and 10 mg compared with placebo using modified OMERACT-OARSI criteria.

In the continuous responder analysis, based on WOMAC pain subscale scores, a higher percentage of subjects in the Meloxicam Capsules 5 mg and 10 mg groups experienced reductions in WOMAC pain subscale scores with a clear separation of the curves for Meloxicam Capsules 5 mg and 10 mg treatment groups compared with placebo at each trial visit.

Patient-reported outcomes provide an important measure of the clinical significance of observed treatment benefits from the subject's perspective. More subjects in both the Meloxicam Capsules 5 mg treatment group (50.0%) and 10 mg treatment group (52.8%) assessed their overall status as "very much improved" or "much improved" following treatment with trial drug. This is in contrast to only 40.0% of subjects in the placebo group.

Physicians assessed the overall status of subjects as "very much improved" or "much improved" for the majority of subjects receiving Meloxicam Capsules: 51.1% of subjects in the Meloxicam Capsules 5 mg treatment group and 52.8% of subjects in the Meloxicam Capsules 10 mg treatment group. This is in contrast to the placebo group, where only 38.5% of physicians rated subjects' overall status as "very much improved" or "much improved." Assessments of "very much improved" and "much improved" indicate clinically significant treatment benefits and improvements in overall symptoms associated with OA.

In secondary efficacy analyses, the patient global impression of change (PGIC) and the clinical global impression of change (CGIC) from Baseline to Week 12 were generally positive by both measures as indicated above. Meloxicam Capsules 5 mg and 10 mg both demonstrated significant differences compared with placebo in the overall response patterns for the PGIC (P=0.0049 and P=0.0012, respectively) and the CGIC (P=0.0070 and P=0.0013, respectively). These results indicate that subjects on both dosing regimens derived an overall treatment benefit compared with placebo as evidenced by favorable overall impressions of their change in status at Week 12 compared with Baseline.

The LS mean daily rescue medication usage was lowest in the Meloxicam Capsules 10 mg treatment group (313.6 mg, P=0.0024 vs placebo). Subjects in the Meloxicam Capsules 5 mg treatment group (LS mean 25.3 days, P=0.0007 vs placebo) and Meloxicam Capsules 10 mg treatment group (LS mean 23.5 days, P<0.0001 vs placebo) demonstrated fewer average number of days of rescue medication usage compared with the placebo group (LS mean 33.9 days).

Post hoc analyses examined rescue medication usage in relation to time of day (over four 6-hour intervals) and elapsed treatment duration (number of days on the trial). These analyses generally showed a gradual decrease in the amount of rescue medication usage as the number of days on trial medication increased, across all treatment groups. Additionally, post hoc analyses demonstrated rescue medication usage was lower among Meloxicam Capsules subjects compared with placebo for most time intervals throughout the treatment period. Rescue medication usage during the evening hours was lower for Meloxicam Capsules subjects compared with placebo, with most robust differences noted for those subjects in the 10 mg treatment group.

An exploratory analysis evaluated whether the PK properties of Meloxicam Capsules might be associated with a measurable impact on analgesia following administration of the morning dose at a time corresponding to the observed maximum plasma concentration (2 hours). Subjects in the Meloxicam Capsules 5 mg and 10 mg treatment groups and the placebo group assessed their OA pain using the 11-point NPRS on a single day within 1 week of completion of the Week 2 Visit at predose, and 2-hour postdose time points. Subjects in the Meloxicam Capsules 5 mg and 10 mg treatment groups demonstrated a greater percentage reduction in the NPRS score compared with placebo. Substantial differences vs placebo in the raw mean change and LS mean change in NPRS score from predose to postdose assessment were noted in the Meloxicam Capsules 5 mg group; however, these changes were significant only for the LS Mean analysis for percentage change (P=0.0294). The results for the sensitivity analysis of the exploratory efficacy analysis using BOCF imputation were similar to the first exploratory efficacy analysis.

Overall, once daily Meloxicam Capsules 5 mg and 10 mg were generally well tolerated. The number and type of TEAEs that were reported during the conduct of the trial were expected and typical for this trial population. A total of 113 subjects experienced at least 1 TEAE during the trial. A higher proportion of subjects in the placebo (32.3%) treatment group experienced at least 1 TEAE compared with the 5 mg (25.4%) and 10 mg (26.7%) groups. No subjects in any treatment group experienced an SAE, and no deaths occurred during the conduct of this trial. A total of 3 subjects overall experienced TEAEs considered severe in intensity; a higher proportion of subjects in the placebo treatment group (1.5%) experienced severe TEAEs compared with the Meloxicam Capsules 5 mg (0.0%) and 10 mg (0.8%) groups.

Overall, headache was the most frequently reported TEAE in all subjects (2.7%). Headache and diarrhea were the most common TEAEs in the Combined Meloxicam Capsules group (2.6%), followed by nausea (2.2%). A higher proportion of subjects in the combined Meloxicam Capsules group reported nausea (2.2%) and diarrhea (2.6%) when compared with subjects in the placebo group (0.0% and 0.8%, respectively). Headache (3.8%) and abdominal discomfort (2.3%) occurred with higher frequency in the Meloxicam Capsules 10 mg group while exacerbation of OA (2.9%) was observed more frequently in the Meloxicam Capsules 5 mg group. All other TEAEs appeared to be reported by similar proportions of subjects across treatment groups.

Twelve subjects discontinued trial drug due to a TEAE. A total of 6 subjects in the 2 active treatment groups and 6 subjects in the placebo group experienced events leading to trial drug discontinuation.

Vital sign values, hematology laboratory values, urinalysis laboratory values, physical examination findings, and ECG findings were generally normal, stable, and similar across treatment groups. Clinically significant changes in some chemistry laboratory values (alkaline phosphatase, ALT, AST, bilirubin, BUN, creatinine, glucose, and potassium) were observed, some of which had TEAEs associated with them, but none of which were considered serious.

Overall, the primary, secondary, and post hoc analyses provide substantial evidence of efficacy for Meloxicam Capsules 5 mg and 10 mg administered once daily for the treatment of OA-related pain. Although results indicating a dose response for Meloxicam were noted for some but not for all efficacy assessments, evidence of a dose effect was demonstrated across multiple secondary and post hoc analyses including use of rescue medication, withdrawal due to lack of efficacy, a modified OMERACT-OARSI responder analysis, and clinician- and subject-reported outcomes.

Safety results indicate that Meloxicam Capsules 5 mg and 10 mg are generally well tolerated with a safety profile that is consistent with the known safety profile of Meloxicam. Importantly, there were no significant cardiovascular, GI, or renal TEAEs of the type that have been associated with NSAID usage in any treatment group.

Taken together, the results of this trial highlight the treatment benefit of once daily Meloxicam Capsules 5 mg and 10 mg for the treatment of pain associated with OA symptoms. Additionally, treatment with Meloxicam Capsules also appears to provide meaningful improvements in other symptoms of OA, namely improvements in function, stiffness, and overall status.

What is claimed is:

1. A method for treating osteoarthritis comprising administering a capsule form of a pharmaceutical composition comprising 5 mg of meloxicam having a median particle size, on a volume basis, between 100 nm and 1000 nm, wherein a single dose, upon oral administration to a population of healthy adults in the fasted state, provides a mean plasma AUC (0-∞) of 7500-20000 h*ng/ml and a mean plasma Cmax of 350-950 ng/ml, wherein the D(0.9) of the particles of meloxicam is less than 4000 nm and greater than 1200 nm, and wherein the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 80% of the meloxicam dissolves in 10 minutes or less.

2. The method of claim 1, wherein the dissolution rate is such that, when tested using USP Apparatus 1 (baskets) set to rotation speed of 100 RPM in 500 mL of pH 6.1 phosphate buffer with 0.1% sodium lauryl sulfate (SLS) at 37° C.±0.5° C., at least 90% of the meloxicam dissolves in a time period selected from: 8 minutes or less; 7 minutes or less; 6 minutes or less; and 5 minutes or less.

3. The method of claim 1, wherein a single dose, upon oral administration to a population of healthy adults in the fasted state, provides a median plasma Tmax of 1 to 3 hrs.

4. The method of claim 2, wherein a single dose, upon oral administration to a population of healthy adults in the fasted state, provides a median plasma Tmax of 1 to 3 hrs.

5. The method of claim 1, wherein a single dose, upon oral administration to a population of healthy adults in the fasted state, provides a mean plasma AUC (0-∞) that is 80% to 125% of 13610 ng-h/ml.

6. The method of claim 2, wherein a single dose, upon oral administration to a population of healthy adults in the fasted state, provides a mean plasma AUC (0-∞) that is 80% to 125% of 13610 ng-h/ml.

7. The method of claim 1, wherein a single dose, upon oral administration to a population of healthy adults in the fasted state, provides a mean plasma Cmax that is 80% to 125% of 1253 ng/ml.

8. The method of claim 2, wherein a single dose, upon oral administration to a population of healthy adults in the fasted state, provides a mean plasma Cmax that is 80% to 125% of 1253 ng/ml.

9. A method for treating osteoarthritis comprising administering a capsule form of a pharmaceutical composition comprising 10 mg of meloxicam having a median particle size, on a volume basis, between 100 nm and 1000 nm, wherein a single dose, upon oral administration to a population of healthy adults in the fasted state, provides a mean plasma AUC (0-∞) of 16000-44000 h*ng/ml and a mean blood plasma Cmax of 700-1900 ng/ml, wherein the D(0.9) of the particles of meloxicam is less than 4000 nm and greater than 1200 nm, and wherein the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 80% of the meloxicam dissolves in 15 minutes or less.

10. The method of claim 9 wherein the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 90% of the meloxicam dissolves in a time period selected from: 14 minutes or less; 13 minutes or less; 12 minutes or less; 11 minutes or less; 10 minutes or less; and 5 minutes or less.

11. The method of claim 9, wherein a single dose, upon oral administration to a population of healthy adults in the fasted state, provides a median plasma Tmax of 1 to 3 hrs.

12. The method of claim 10, wherein a single dose, upon oral administration to a population of healthy adults in the fasted state, provides a median plasma Tmax of 1 to 3 hrs.

13. The method of claim 9, wherein a single dose, upon oral administration to a population of healthy adults in the fasted state, provides a mean plasma AUC (0-∞) that is 80% to 125% of 29,173 ng-h/ml.

14. The method of claim 10, wherein a single dose, upon oral administration to a population of healthy adults in the fasted state, provides a mean plasma AUC (0-∞) that is 80% to 125% of 29,173 ng-h/ml.

15. The method of claim 9, wherein a single dose, upon oral administration to a population of healthy adults in the fasted state, provides a mean plasma Cmax that is 80% to 125% of 1253 ng/ml.

16. The method of claim 10, wherein a single dose, upon oral administration to a population of healthy adults in the fasted state, provides a mean plasma Cmax that is 80% to 125% of 1253 ng/ml.

17. A method for treating osteoarthritis comprising administering a capsule form of a pharmaceutical composition comprising 10 mg of meloxicam having a median particle size, on a volume basis, between 100 nm and 1000 nm, wherein a single dose, upon oral administration to a population of healthy adults in the fed state, provides a mean plasma Cmax of 525-1500 ng/ml and a mean plasma AUC (0-∞) of 15000-42000 h*ng/ml, wherein the D(0.9) of the particles of meloxicam is less than 4000 nm and greater than 1200 nm, and wherein the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 80% of the meloxicam dissolves in 15 minutes or less.

18. The method of claim 17, wherein the dissolution rate is such that, when tested using USP Apparatus 1 (baskets) set to rotation speed of 100 RPM in 1000 mL of pH 6.1 phosphate buffer with 0.1% sodium lauryl sulfate (SLS) at 37° C.±0.5° C., at least 90% of the meloxicam dissolves in a time period selected from: 14 minutes or less; 13 minutes or less; 12 minutes or less; 11 minutes or less; 10 minutes or less; and 5 minutes or less.

19. The method of claim 17, wherein a single dose, upon oral administration to a population of healthy adults in the fed state, provides a median plasma Tmax of 3 to 7 hrs.

20. The method of claim 18, wherein a single dose, upon oral administration to a population of healthy adults in the fed state, provides a median plasma Tmax of 3 to 7 hrs.

21. The method of claim 17, wherein a single dose, upon oral administration to a population of healthy adults in the fed state, provides a mean plasma Cmax that is 80% to 125% of 974 ng/ml.

22. The method of claim 18, wherein a single dose, upon oral administration to a population of healthy adults in the fed state, provides a mean plasma Cmax that is 80% to 125% of 974 ng/ml.

23. The method of claim 17, wherein a single dose, upon oral administration to a population of healthy adults in the fed state, provides a mean plasma AUC(0-∞) that is 80% to 125% of 27,146 ng/ml.

24. The method of claim 18, wherein a single dose, upon oral administration to a population of healthy adults in the fed state, provides a mean plasma AUC(0-∞) that is 80% to 125% of 27,146 ng/ml.

\* \* \* \* \*